US00PP17709P2

(12) United States Plant Patent
Austin

(10) Patent No.: US PP17,709 P2
(45) Date of Patent: May 8, 2007

(54) SHRUB ROSE PLANT NAMED 'AUSBROTHER'

(50) Latin Name: *Rosa hybrida*
Varietal Denomination: AUSbrother

(75) Inventor: David C. H. Austin, Albrighton (GB)

(73) Assignee: David Austin Roses Limited, Albrighton, Wolverhampton (GB)

( * ) Notice: Subject to any disclaimer, the term of this patent is extended or adjusted under 35 U.S.C. 154(b) by 0 days.

(21) Appl. No.: 11/250,602

(22) Filed: Oct. 13, 2005

(51) Int. Cl.
*A01H 5/00* (2006.01)

(52) U.S. Cl. ..... Plt./105
(58) Field of Classification Search ..... Plt./105
See application file for complete search history.

*Primary Examiner*—Kent Bell
*Assistant Examiner*—June Hwu
(74) *Attorney, Agent, or Firm*—Klarquist Sparkman LLP

(57) ABSTRACT

Shrub rose plant characterized particularly by its deeply cupped blooms, tangerine-orange on inner side and yellow-orange on the reverse; very strong and complex fruity fragrance; and bronzy-green young foliage becoming dark green on upright, bushy growth.

1 Drawing Sheet

Genus and Species: *Rosa hybrida.*
Variety Denomination: 'AUSbrother'.

ORIGIN OF THE INVENTION

The present invention relates to a new and distinct variety of a shrub rose plant named 'AUSbrother' which was originated by me by crossing an unnamed, unpatented seedling with an unnamed, unpatented seedling.

BACKGROUND OF THE INVENTION

The primary objective of this invention was to produce a rose plant having very free-flowering and healthy, tangerine-orange blooms with a yellow-orange reverse and a strong fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Deeply cupped blooms, tangerine-orange on inner side and yellow-orange on the reverse.
2. Very strong and complex fruity fragrance.
3. Bronzy-green foliage becoming dark green on upright, bushy growth.

Asexual reproduction of this new variety by budding, as performed at Albrighton, England, shows that the foregoing and all other characteristics and distinctions come true to form and are established and transmitted through succeeding propagations.

COMPARISON WITH PARENTS

The seed parent has apricot, rosette-shaped blooms compared to the bright yellow-orange, cupped blooms of 'AUSbrother', and the foliage of the seed parent is less bronzy than that of 'AUSbrother'. The pollen parent has less petalage than 'AUSbrother' and the blooms are paler orange in color.

COMPARISON WITH SIMILAR VARIETY

'AUSmum' (U.S. Plant Pat. No. 9,527), the most similar variety, has larger, brighter orange blooms than 'AUSbrother' and fewer small prickles. 'AUSbrother' has a more upright growth and a stronger fragrance than 'AUSmum'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling (Unpatented).

FLOWER

Observations made from plants asexually reproduced by budding, commencing at one year of age grown in a garden environment at Albrighton, England.

Blooming habit: Recurrent. The number of blooms per plant during the growing season is profuse; there are too many to count.

Bud:
*Size.*—About 2.6 cm long and 2 cm in diameter when the petals start to unfurl.
*Form.*—The bud form is pointed ovoid.
*Color.*—When sepals first divide, bud color is Red Group 45B. When half blown, the upper sides of the petals are Orange Group 28A; and the lower sides of the petals are Yellow-Orange Group 22B (base and margin) and Orange Group 24C (central area).

*Sepals.*—Color: Upper surface: Greyed-Red Group 183C at base and margin and Greyed-Red Group 181B in the central area. Lower surface: Yellow-Green Group 148C and Yellow-Green Group 144C at base. Length: 2.4 cm. Width: 1.2 cm. Shape: Subulate. Surface texture: Upper surface: Glandular Lower surface: Pubescent. There are three lightly appendaged sepals. There are two unappendaged sepals with canescent edges.

*Receptacle.*—Color: Yellow-Green Group 144A with irregular patches of Greyed-Purple Group 183B. Shape: Campanulate. Size: Medium, about 0.7 cm long×1 cm wide. Surface: Smooth.

*Peduncle.*—Length: Medium, averaging about 6 cm. Surface: Prickly Color: Orange-Red Group N34C. Strength: Strong.

Bloom:

*Size.*—Large. Average open diameter is about 8.7 cm.

*Borne.*—Several together in rounded clusters of four to seven blooms.

*Form.*—When first open: Cupped. Permanence: Retains its form to the end.

*Petalage.*—Number of petals under normal conditions: 46.

*Color.*—The upper sides of the petals are Orange Group 26C (margin and upper zone) and Yellow-Orange Group 20B (middle zone to base). The reverse sides of the petals are Yellow-Orange Group 20B (margin and upper zone) and 20C (middle zone to base). The base of each petal is Yellow Group 7D. The undersides of some of the very outer petals have markings of Red Group 47A and Red Group 51A, which are normally concentrated in the central portion of the petal and spread outwards.

*Variegations.*—None.

*Discoloration.*—The general tonality at the end of the first day: Overall bloom color varies between Yellow-Orange Group 22C and Orange Group 24D. At the end of the third day: Overall bloom color varies between Yellow-Orange Group 23D and Yellow Group 9C.

*Fragrance.*—Strong, fruity.

Petals:

*Texture.*—Smooth.

*Size.*—Width: 3.5 cm. Length: 4.6 cm.

*Surface.*—Smooth.

*Shape.*—Obcordate. Margin: Flat, slightly reflexing, mainly on outer petals. Apex Shape: Obcordate. Base Shape: Cuneate (outer petals blunt tipped). Form: Incurved (tips slightly recurved on some).

*Arrangement.*—Imbricated, regularly arranged, shingle-like.

*Petaloids.*—Number: 6. Color: Anther: Orange Group 28C. Filament: Yellow Group 9B. Petal: Upper surface: Orange Group 29A with Yellow Group 7B towards base and margin bearing the anther, and Orange Group 29B on reverse side and Yellow Group 7B towards base and margin bearing the anther.

*Persistence.*—Petals drop off cleanly before drying.

*Lastingness.*—On the plant: Fair (about 4 days). As a cut flower: Fair (about 5 days).

Reproductive parts:

*Stamens.*—Number: 137. Length: 7 mm. Anthers: Length: 2 mm. Color: Orange Group 9A. Arrangement: Regular around styles, mixed with petaloids. Filaments: Color: Yellow-Orange Group 16A. Length: 5 mm. Pollen: Color: Yellow Group 9A.

*Pistils.*—Number: 96. Length: 8 mm. Styles: Color: Green-Yellow Group 1D. Length: 7 mm. Stigmas: Color: Yellow-Orange Group 22D with pink edge not concentrated enough to determine RHS color code. Length: 1 mm.

*Hips.*—None observed.

PLANT

*Form.*—Shrub.

*Growth.*—Medium vigor, bushy.

*Age at maturity.*—Two years.

*Mature plant.*—Height: 1.25 m. Width: 0.9 m.

*Rootstock.*—*Rosa dumetorum* 'Laxa' for the observed plants in the U.K. 'Dr. Huey' in the USA.

Foliage: Number of leaflets on normal mid-stem leaves: 5–7 (including terminal leaflet).

*Size.*—Medium. About 17.6 cm long×11.9 cm wide.

*Quantity.*—Normal. Average number leaves per flowering stem: 10.

*Color.*—New foliage: Upper side: Yellow-Green Group 146B with Greyed-Purple Group 183A concentrated around margin. Lower side: Greyed-Purple Group 184B. Old foliage: Upper side: Some Yellow-Green Group 147A and some Green Group 137A. Lower side: Yellow-Green Group 147B.

Leaflets:

*Size.*—About 6.9 cm long×4.5 cm wide.

*Shape.*—Oval.

*Base shape.*—Rounded.

*Apex shape.*—Acuminate.

*Texture.*—Leathery.

*Edge.*—Serrated.

*Serrations.*—Single (some double), large.

*Petiole.*—Color: Yellow-Green Group 144D overlaid with brown/red tint on upper side (not concentrated enough to determine RHS color code). Surface Texture: Smooth. Length: Approximately 3.5 cm. Width: Approximately 1–2 mm, depending upon leaf maturity.

*Petiole rachis.*—Color: Green Group 142D. Underside: Smooth.

*Stipules.*—Length: 3.5 cm, serrated (highly). Color: Yellow-Green Group 144A on mature leaf; Yellow-Green Group 146B overlaid with Grey-Purple Group 183D on new leaf.

*Auricles.*—Shape: Subulate. Length: 5–8 mm, depending upon leaf size. Width: Approximately 1 mm at the base, tapering to a fine point.

*Disease resistance.*—Resistant to powdery and downy mildew, blackspot and rust in normal growing conditions.

*Pest resistance.*—Not tested.

*Vein color.*—Green Group 142D.

*Venation pattern.*—Reticulate.

Wood:

*New wood.*—Color: Red Group 53A and Grey-Brown Group 199B (longitudinal split, equal proportion of stem given to each color). Bark: Smooth (with prickles).

*Old wood.*—Color: Yellow-Green Group 144A. Bark: Smooth.

Stems:

*Mature stem.*—Length: 43 cm. Diameter: 8 mm.

*Internode distance.*—4.5 cm.

The above measurements are all variable depending on growing conditions in a season.

Prickles:

*Quantity.*—On main canes from base: 7 per 5 cm stem length. On laterals from main canes: 7 per 5 cm per stem length.

*Form.*—Deep concave.

*Length.*—9 mm.

*Color when young.*—Greyed-Purple Group 185A.

*Color when mature.*—Yellow-Green Group N144A.

Small prickles:

*Quantity.*—On main stalks: 30 per 5 cm. On laterals: 30 per 5 cm.

*Color.*—When young: Greyed-Purple Group 185A. When mature: Yellow-Green Group N144A.

Winter hardiness: Not tested.

I claim:

1. A new and distinct variety of rose plant of the shrub class, substantially as herein shown and described, characterized particularly by its deeply cupped blooms, tangerine-orange on inner side and yellow-orange on the reverse; very strong and complex fruity fragrance; and bronzy-green young foliage becoming dark green on upright, bushy growth.

* * * * *

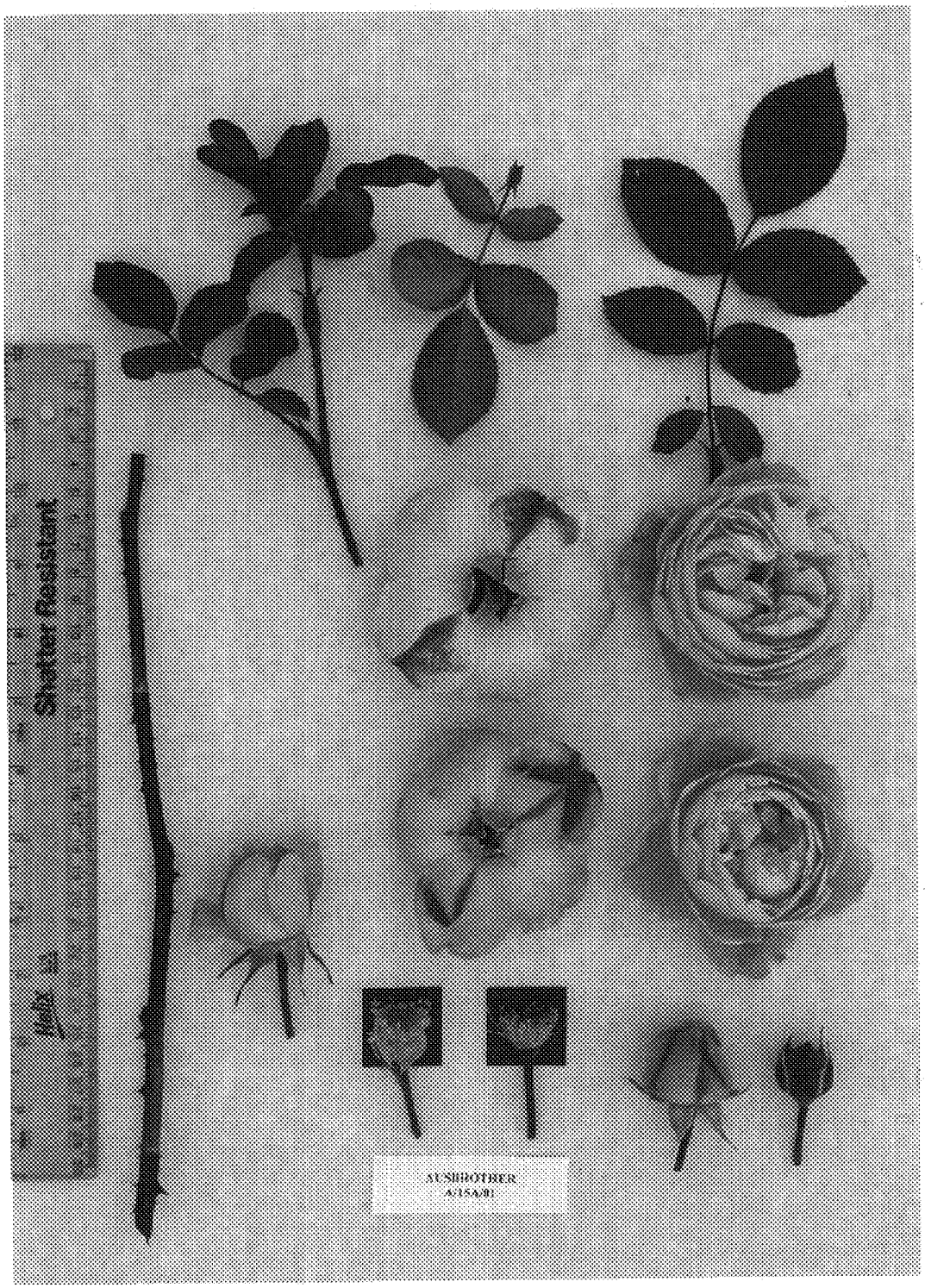
Shatter Resistant
AUSBROTHER
A/15A/81